United States Patent
Nakatani et al.

(10) Patent No.: US 10,017,485 B2
(45) Date of Patent: Jul. 10, 2018

(54) MANUFACTURING METHOD FOR COMPOUND HAVING N,N-BIS(2-HYDROXY-3-CHLOROPROPYL)AMINO GROUP

(71) Applicant: Toray Fine Chemicals Co., Ltd., Tokyo (JP)

(72) Inventors: Jiro Nakatani, Mroiyama (JP); Ryota Takezawa, Moriyama (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 15/549,217

(22) PCT Filed: Feb. 8, 2016

(86) PCT No.: PCT/JP2016/053698
§ 371 (c)(1),
(2) Date: Aug. 7, 2017

(87) PCT Pub. No.: WO2016/129561
PCT Pub. Date: Aug. 18, 2016

(65) Prior Publication Data
US 2018/0030013 A1   Feb. 1, 2018

(30) Foreign Application Priority Data
Feb. 13, 2015   (JP) .................. 2015-026548

(51) Int. Cl.
*C07D 301/27*   (2006.01)
*C07C 213/02*   (2006.01)

(52) U.S. Cl.
CPC .......... *C07D 301/27* (2013.01); *C07C 213/02* (2013.01)

(58) Field of Classification Search
CPC .................. C07D 301/27; C07C 213/02
See application file for complete search history.

(56) References Cited

U.S. PATENT DOCUMENTS

2015/0298095 A1* 10/2015 Ashe .................. B01F 5/0619
423/659

FOREIGN PATENT DOCUMENTS

| GB | 1578303 | * 11/1980 |
| JP | 53-124226 A | 10/1978 |
| JP | 04-145054 A | 5/1992 |
| JP | 2009-203425 A | 9/2009 |
| JP | 2012-219081 A | 11/2012 |
| JP | 2013-193980 A | 9/2013 |
| WO | 2013/089006 A1 | 6/2013 |
| WO | 2014/162947 A1 | 10/2014 |

OTHER PUBLICATIONS

WO/2013089006 ProQuest Dialog English machine translation p. 1-28.*
Henkel, K., "Reactor types and their industrial applications." Ullmann's Encyclopedia of Industrial Chemistry (2000).*
V. Getautis et al., "Study of the Products from Reaction of 1(2)-Aminoanthraquinones with 1-Chloro-2,3-Epoxypropane," Chemistry of Heterocyclic Compounds, Apr. 2005, vol. 41, Issue 4, pp. 426-436 (Abstract).

* cited by examiner

*Primary Examiner* — John M Mauro
(74) *Attorney, Agent, or Firm* — DLA Piper LLP (US)

(57) ABSTRACT

A method efficiently and safely manufactures, on an industrial scale, a compound having an N,N-bis(2-hydroxy-3-chloropropyl)amino group. (1) an amine compound or a solution thereof, (2) epichlorohydrin or a solution thereof, and (3) an acidic compound or a solution thereof are continuously supplied to a flow reactor and reacted at a reaction temperature of 40 to 130° C. and a liquid space velocity of 0.2 to 10 $h^{-1}$ so that a compound having an N,N-bis(2-hydroxy-3-chloropropyl)amino group is manufactured. The obtained compound having an N,N-bis(2-hydroxy-3-chloropropyl)amino group is dehydrochlorinated by reaction with an alkali so that a polyfunctional glycidylamine type epoxy compound is manufactured.

15 Claims, 1 Drawing Sheet

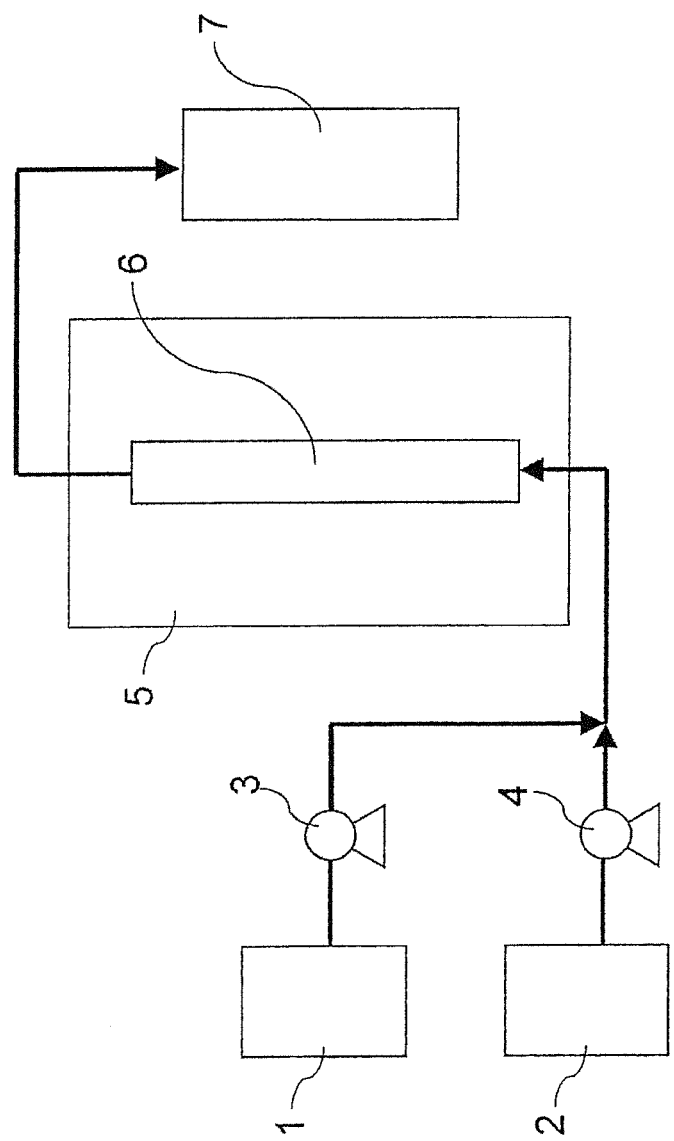

MANUFACTURING METHOD FOR COMPOUND HAVING N,N-BIS(2-HYDROXY-3-CHLOROPROPYL)AMINO GROUP

TECHNICAL FIELD

This disclosure relates to a manufacturing method for a compound having an N,N-bis(2-hydroxy-3-chloropropyl) amino group that is industrially useful, high in production efficiency and high in safety.

BACKGROUND

A compound having an N,N-bis(2-hydroxy-3-chloropropyl)amino group is useful as an intermediate for polyfunctional glycidylamine based epoxy compounds. Polyfunctional glycidylamine based epoxy compounds derived from a compound having an N,N-bis(2-hydroxy-3-chloropropyl) amino group are compounds widely used in the organic chemistry and polymer chemistry fields and compounds useful in diverse fields for industrial uses as fine chemicals, raw materials of pharmaceuticals and agricultural chemicals, and raw materials of resins as well as electronic information materials, optical materials and the like.

Furthermore, polyfunctional glycidylamine type epoxy compounds, when hardened by various hardening agents, generally make hardened materials excellent in mechanical properties, water resistance, chemical resistance, heat resistance, and electrical characteristics, and are utilized in a wide variety of fields such as adhesives, paints, laminates, and composite materials.

A manufacturing method for a common polyfunctional glycidylamine type epoxy compound is carried out by producing a compound having an N,N-bis(2-hydroxy-3-chloropropyl)amino group through an addition reaction between an amine compound and epichlorohydrin in a batch type reaction scheme and causing a cyclization reaction of the production through dehydrochlorination with an alkali.

However, if the addition reaction between an amine compound and epichlorohydrin is carried out by a batch type reaction scheme, rapid heat generation is often involved and, if a reaction accelerating agent such as a catalyst is added to increase the reaction rate, rapid heat generation occurs, leading to a risk of a runaway of the reaction.

Therefore, Japanese Examined Patent Publication (Kokoku) No. SHO 53-124226 proposes a method using a batch type reaction apparatus equipped with a cooling hose within a reaction vessel and in which after epichlorohydrin and water are charged thereinto, an amine compound is gradually dropped while heat is removed to maintain an appropriate reaction temperature.

International Publication WO 2013/089006 proposes a method in which a reaction accelerating agent such as an organic acid is slowly dropped into a system in which an amine compound has been dissolved in epichlorohydrin.

Meanwhile, Japanese Unexamined Patent Publication (Kokai) No. 2009-203425 discloses a method in manufacture of glycidyl ethers which, using a solid acid catalyst, manufactures chlorohydrin ether, an intermediate for a glycidyl ether, in a fixed-bed flow scheme.

However, in the manufacturing method for a polyfunctional glycidylamine type epoxy compound described in JP '226, since the amine compound is dropped while the reaction is controlled, the dripping time is long and, furthermore, to remove reaction heat, a special reaction apparatus equipped with a cooling hose within the reaction vessel is necessary. Furthermore, in the method described in WO '006 in which a reaction accelerating agent is slowly dropped into a system in which an amine compound has been dissolved in epichlorohydrin, if the dripping speed of the reaction accelerating agent is great, the reaction immediately progresses, leading to a risk of a runaway of the reaction so that there is a need to sufficiently control the dripping speed of the reaction accelerating agent. Thus, the method has a problem as a safe industrial manufacturing method.

Meanwhile, if the addition reaction between an amine compound and epichlorohydrin is carried out in a fixed-bed flow by using the solid acid catalyst as described in JP '425, the reaction progresses in an early period of the reaction but gradually decreases in the reaction rate. The decreases occur because amine, which is a reaction substrate, comes to remain adsorbed to acid points on the solid acid catalyst which are reaction activity points so that the acid points are poisoned. Hence, if the solid acid catalyst is used in the fixed-bed flow reaction, the reaction does not stabilize and, furthermore, the catalyst loses activity in a short time so that the catalyst is frequently replaced, posing a problem for stable industrial production.

That is, in manufacture of a compound having an N,N-bis(2-hydroxy-3-chloropropyl)amino group, an industrial manufacturing method that is high in production efficiency and high in safety has not been established yet.

Therefore, a manufacturing method that efficiently and safely produces on an industrial scale a compound having an N,N-bis(2-hydroxy-3-chloropropyl)amino group has been demanded.

It could therefore be helpful to provide a method of manufacturing a compound having an N,N-bis(2-hydroxy-3-chloropropyl)amino group highly efficiently and safely on an industrial scale.

SUMMARY

We found in a manufacturing method for a compound having an N,N-bis(2-hydroxy-3-chloropropyl)amino group a method of manufacturing a compound having an N,N-bis(2-hydroxy-3-chloropropyl)amino group in which (1) an amine compound or a solution thereof, (2) epichlorohydrin or a solution thereof, and (3) an acidic compound or a solution thereof are continuously supplied to a flow reactor and reacted at a reaction temperature of 40 to 130° C. and a liquid space velocity of 0.2 to 10 $h^{-1}$.

According to the manufacturing method, by continuously supplying (1) an amine compound or a solution thereof, (2) epichlorohydrin or a solution thereof, and (3) an acidic compound and a solution thereof to a flow reactor in an addition reaction between the amine compound and epichlorohydrin, a compound having an N,N-bis(2-hydroxy-3-chloropropyl)amino group can be continuously produced so that productivity can be considerably improved compared to related-art methods.

Furthermore, in a flow reactor, by adjusting the supply velocities of (1) the amine compound or a solution thereof, (2) epichlorohydrin or a solution thereof, and (3) the acidic compound and a solution thereof, the reaction can be controlled. Furthermore, by causing the reaction liquid to flow, heat and substances diffuse rapidly so that accumulation of reaction heat becomes less, enabling the safe and industrial manufacturing that can avoid the risk of a runaway resulting from a chain-like reaction.

BRIEF DESCRIPTION OF THE DRAWINGS

The Figure is a flow diagram illustrating an example of an apparatus used in our manufacturing method.

EXPLANATION OF NUMERALS

1 Reaction raw material liquid
2 Reaction accelerating agent
3 Reaction raw material liquid delivery pump
4 Reaction accelerating agent liquid delivery pump
5 Constant temperature tank
6 Tubular reactor
7 Reaction liquid receiver

DETAILED DESCRIPTION

The manufacturing method for a compound having an N,N-bis(2-hydroxy-3-chloropropyl)amino group will be described in detail hereinafter. Incidentally, in this description, the "compound having an N,N-bis(2-hydroxy-3-chloropropyl)amino group" is an amine compound having one or more N,N-bis(2-hydroxy-3-chloropropyl)amino groups; for example, an N,N-bis(2-hydroxy-3-chloropropyl)amine compound, an N,N,N',N'-tetra(2-hydroxy-3-chloropropyl) diamine compound or the like can be cited.

The manufacturing method for a compound having an N,N-bis(2-hydroxy-3-chloropropyl)amino group is an addition reaction method that obtains a compound having an N,N-bis(2-hydroxy-3-chloropropyl)amino group by continuously supplying (1) an amine compound or a solution thereof, (2) epichlorohydrin or a solution thereof, and (3) an acidic compound or a solution thereof as a reaction accelerating agent to a flow reactor.

The manufacturing method is characterized by continuously carrying out an addition reaction of an amine compound and epichlorohydrin in the presence of an acidic compound through the use of a flow reactor.

As an amine compound, a monoamine compound and a diamine compound can be used. As the monoamine compound, for example, aniline, o-toluidine, m-toluidine, p-toluidine, 2-phenoxy aniline, 3-phenoxy aniline, 4-phenoxy aniline, 2-amino phenol, 3-amino phenol, 4-amino phenol and the like are presented as examples. By carrying out an addition reaction of epichlorohydrin with a monoamine, an N,N-bis(2-hydroxy-3-chloropropyl)amine compound is obtained. As the monoamine compound, aniline, toluidine, phenoxy aniline, and amino phenol are preferable and, in particular, aniline, o-toluidine, m-toluidine, 4-phenoxy aniline, 3-amino phenol, and 4-amino phenol are preferable.

Meanwhile, when a diamine compound is used as an amine compound and epichlorohydrin is caused to undergo an addition reaction with the amine compound, an N,N,N',N'-tetra(2-hydroxy-3-chloropropyl)diamine compound is obtained. As the diamine compound, for example, 4,4'-diaminodiphenyl methane, 3,3'-diaminodiphenyl methane, 3,4'-diaminodiphenyl methane, 4,4'-diaminodiphenyl ether, 3,3'-diaminodiphenyl ether, 3,4'-diaminodiphenyl ether, 4,4'-diaminodiphenyl sulphone, 3,3'-diaminodiphenyl sulphone, 3,4'-diaminodiphenyl sulphone or the like can be cited. As the diamine compound, diaminodiphenyl ether, diaminodiphenyl methane, and diaminodiphenyl sulphone are preferable and, in particular, 4,4'-diaminodiphenyl methane, 4,4'-diaminodiphenyl ether, 3,4'-diaminodiphenyl ether, 4,4'-diaminodiphenyl sulphone, and 3,3'-diaminodiphenyl sulphone are preferable.

In the method, when the amine compound is in a liquid state, the amine compound may be used as it is or may be diluted in epichlorohydrin or a solvent for use. When the amine compound is a solid, the amine compound may be dissolved in epichlorohydrin or a solvent to form a solution or may also be used in the form of a slurry liquid. In any case, it is preferable that the amine compound be supplied in a solution or a slurry solution to the flow reactor.

Epichlorohydrin, which is reacted with an amine compound, may be supplied as it is or may also be diluted in a solvent for use.

The amount of epichlorohydrin supplied is 1 to 20 times by mole relative to the amount of the amine compound supplied to the flow reactor and, more preferably, 2 to 10 times by mole.

In the method, an acidic compound is used as a reaction accelerating agent. As the acidic compound, Lewis acids and organic acids can be cited. As concrete examples of the Lewis acid, substances capable of accepting an electron pair, more concretely, boron trifluoride, boron trifluoride-diethyl ether complex, boron trichloride, boron tribromide, magnesium chloride, magnesium bromide, aluminum trichloride, aluminum bromide, zinc chloride, tin chloride (IV), iron chloride (III), antimony fluoride (V), antimony chloride (V), phosphorus trichloride, phosphorus pentachloride, phosphorus oxychloride, titanium tetrachloride, titanium trichloride, vanadyl chloride [$VOCl_2$], zirconium chloride, hafnium chloride, tetraisopropoxy titanium, trifluoromethane scandium sulfonate (III), niobium trichloride, and niobium pentachloride can be cited, and it is preferable to use tin chloride (IV), iron chloride (III), titanium tetrachloride, aluminum trichloride, zirconium chloride, tetraisopropoxy titanium, boron trifluoride, and boron trifluoride-diethyl ether complex, which are particularly easily available and low in toxicity. More preferable are tin chloride (IV), iron chloride (III), titanium tetrachloride, aluminum trichloride, and zirconium chloride. A solid Lewis acid is dissolved in epichlorohydrin or a solvent and supplied as a Lewis acid-containing solution. A Lewis acid in a liquid state may be supplied as it is or may also be diluted in epichlorohydrin or a solvent for use.

The amount of a Lewis acid supplied is 0.001 to 0.5 time by mole relative to the amount of the amine compound supplied to the flow reactor and, more preferably, 0.01 to 0.1 time the amount by mole.

As concrete examples of the organic acid, for example, formic acid, acetic acid, propionic acid, butyric acid, isobutyric acid, pivalic acid, valeric acid, isovaleric acid, caproic acid, 2-ethylbutyric acid, caprylic acid, 2-ethylhexanoic acid, oleic acid, acetic anhydride, propionic anhydride, butyric anhydride, citric acid, lactic acid, oxalic acid, octylic acid, naphthenic acid, neodecanoic acid, capric acid, lauric acid, myristic acid, palmitic acid, stearic acid, arachidic acid, behenic acid, lignoceric acid, cerotic acid, montanoic acid, melissic acid, obtusilic acid, linderic acid, tsuzuic acid, sperm whale acid, myristoleic acid, zoomaric acid, petroselinic acid, vaccenic acid, gadoleic acid, whale oil acid, erucic acid, shark oil acid, linolic acid, Hirago acid, eleostearic acid, punic acid, tricosane acid, linolenic acid, Morokuchi acid, parinaric acid, arachidonic acid, clupanodonic acid, milkshark acid, herring acid or the like can be cited. In particular, formic acid, acetic acid, propionic acid, butyric acid, and isobutyric acid are preferable; more preferably, acetic acid and propionic acid are used. When the organic acid is a solid, the organic acid may be dissolved in epichlorohydrin or a solvent and supplied in the form of an organic acid-containing solution. When the organic acid is a liquid, the organic acid may be supplied as it is, or may also be diluted in epichlorohydrin or a solvent or the like and supplied.

The amount of organic acid supplied is 0.01 to 20 times by weight and, more preferably, 0.05 to 10 times by weight relative to the amount of the amine compound supplied to the flow reactor.

In the reaction, a no-solvent manner is permissible or a solvent may be used as long as the solvent inhibits a reaction between the amine compound and epichlorohydrin. When the amine compound and the acidic compound are solids, a solvent may be used to prepare them in the form of a solution.

As a solvent used in the reaction, an alcohol based solvent, a hydrocarbon based solvent, an ether based solvent, and an ester based solvent are preferably used. Concretely, as the alcohol based solvent, primary alcohols such as methanol, ethanol, 1-propanol, 1-butanol, 1-pentanol, and 1-hexanol, secondary alcohols such as isopropanol, 2-butanol, 2-pentanol, 3-pentanol, 2-hexanol, cyclohexanol, 2-heptanol, and 3-heptanol, tert-butanol, tert-pentanol, ethylene glycol, and propylene glycol can be cited.

As the hydrocarbon based solvent, hexane, 2-methyl pentane, 2,2-dimethylbutane, 2,3-dimethylbutane, heptane, octane, isooctane, nonane, trimethyl hexane, decane, dodecane, benzene, toluene, xylene, ethyl benzene, cumene, mesitylene, cyclohexyl benzene, diethyl benzene, cyclopentane, methyl cyclopentane, cyclohexane, methyl cyclohexane, ethyl cyclohexane and the like can be cited.

Furthermore, as the ether based solvent, diisopropyl ether, dibutyl ether, dihexyl ether, anisole, phenetole, diphenyl ether, tetrahydrofuran, tetrahydropyran, ethylene glycol dibutyl ether, diethylene glycol dimethyl ether, diethylene glycol diethyl ether, diethylene glycol dibutyl ether and the like can be cited.

Furthermore, as the ester based solvent, methyl acetate, ethyl acetate, acetic acid propyl, acetic acid isopropyl, butyl acetate, acetic acid isobutyl and the like can be cited.

In particular, solvents preferably used are methanol, ethanol, 1-propanol, 1-butanol, isopropanol, 2-butanol, tert-butanol, cyclohexane, toluene, xylene, ethyl benzene, cumene, mesitylene, and diethyl benzene.

The amount of the supplied solvent is preferably 0.1 to 20 times by weight and more preferably 1 to 10 times by weight relative to the amount of the amine compound supplied to the flow reactor.

The reaction is carried out by continuously supplying (1) an amine compound or a solution thereof, (2) epichlorohydrin or a solution thereof, and (3) an acidic compound or a solution thereof to a flow reactor, through the use of a liquid delivery pump or the like. Furthermore, unless there is a safety problem, it is permissible to mix two of (1) the amine compound or a solution thereof, (2) the epichlorohydrin or a solution thereof, and (3) the acidic compound or a solution thereof and supply the two as one solution to the flow reactor.

The FIGURE is a flow diagram illustrating an example of a construction of a reaction apparatus that is used in the manufacturing method. In the FIGURE., a reaction raw material liquid 1 is a reaction raw material liquid made up of (1) a solution of an amine compound and (2) a solution of epichlorohydrin and a reaction accelerating agent 2 is (3) a solution of an acidic compound. A tubular reactor 6 is installed within a constant temperature tank 5 and is adjusted in temperature. The reaction raw material liquid 1 and the reaction accelerating agent 2 are continuously supplied to the tubular reactor 6 at predetermined flows by a reaction raw material liquid delivery pump 3 and a reaction accelerating agent liquid delivery pump 4. At this time, the supply velocities of the liquid space velocities of the reaction raw material liquid 1 and the reaction accelerating agent 2 are adjusted so that the liquid space velocities thereof in the tubular reactor 6 are 0.2 to 10 $h^{-1}$. Furthermore, the supply velocities of the reaction raw material liquid 1 and the reaction accelerating agent 2 and the temperature of the constant temperature tank are adjusted so that the temperature of the addition reaction is 40 to 130° C. Due to this, the tubular reactor 6 continuously and stably produces a compound having an N,N-bis(2-hydroxy-3-chloropropyl)amino group. The obtained compound having an N,N-bis(2-hydroxy-3-chloropropyl)amino group is continuously transferred to a reaction liquid receiver 7.

It is preferable to that the reaction conditions be set to such conditions that, when a raw material amino compound contained in the reaction liquid having passed through the flow reactor is completely consumed, the remaining amount of an intermediate monoadduct N-(2-hydroxy-3-chloropropyl) amine compound in the case where the amine compound is a monoamine amine compound and an intermediate triadduct N,N,N'-tri(2-hydroxy-3-chloropropyl)diamine compound when the amine compound is a diamine is minimum.

A polyfunctional glycidylamine type epoxy compound obtained by dehydrochlorinating, with an alkali, an addition reaction liquid in which the intermediate N-(2-hydroxy-3-chloropropyl)amine compound or N,N,N'-tri(2-hydroxy-3-chloropropyl)diamine compound remains in a large amount is low in purity. For example, when a hardened article is made by using a low-purity polyfunctional glycidylamine type epoxy compound, physical properties thereof are low. Furthermore, if a polyfunctional glycidylamine type epoxy compound obtained from an addition reaction liquid in which the intermediate N-(2-hydroxy-3-chloropropyl)amine compound or N,N,N'-tri(2-hydroxy-3-chloropropyl)diamine compound remains in a large amount is to be purified, a very complicated operation is needed.

The reaction temperature is normally 40 to 130° C., preferably 50 to 120° C., and more preferably 60 to 115° C. A temperature of 40° C. or higher is preferable from the viewpoint of reaction rate, and a temperature of 130° C. or lower is preferable from the viewpoint of inhibiting side reactions.

In the reaction, (1) the amine compound or a solution thereof, (2) epichlorohydrin or a solution thereof, and (3) the acidic compound or a solution thereof are mixed at an reactor entrance or at an upstream side of the entrance and then supplied into the reactor, and the liquid space velocity of the reaction liquid within the reactor is 0.2 to 10 $h^{-1}$ and, preferably, 0.5 to 5 $h^{-1}$. If the liquid space velocity is less than 0.2 $h^{-1}$, impurification of the compound having an N,N-bis(2-hydroxy-3-chloropropyl)amino group occurs so that the purity of the obtained polyfunctional glycidyl aniline type epoxy compound decreases. Furthermore, the viscosity of the epoxy compound sometimes becomes high. On the other hand, if the liquid space velocity exceeds 10 $h^{-1}$, an unreacted raw material or intermediate remains in a large amount in the reaction liquid.

Incidentally, in this description, the liquid space velocity is determined by the following expression:

The liquid space velocity ($h^{-1}$)=(supply velocity (ml/min) to the reactor)/(actual space volume (ml) of the reactor)×60 (min/h).

In the expression, the "supply velocity (ml/min) to the reactor" is a supply velocity (ml/min) regarding a sum of (1) the amine compound or a solution thereof, (2) epichlorohydrin or a solution thereof, and (3) the acidic compound or a solution thereof combined, and the "actual space volume (ml) of the reactor" is a volume (ml) of water with which the interior of the reactor is filled.

As the flow reactor, a flow reaction having on a side thereof an entrance through which (1) the amine compound or a solution thereof, (2) epichlorohydrin or a solution thereof, and (3) the acidic compound or a solution thereof are introduced and having an exit through which the reaction liquid, after residing in the reactor for a fixed time, comes out at a side opposite to the reactor entrance is mentioned as an example. As for a preferable shape of the reactor, a tubular reaction tube is preferable. The tubular reaction tube mentioned herein refers to a reactor tube whose length (L) and diameter (D) have a ratio (L/D) of 2 or greater.

Furthermore, as for the flow reactor, it is preferable that the reactor be charged with a filler that is not involved in the reaction to accelerate matter transfer and heat transfer in the reaction liquid, that is, enhance the stirring effect.

Incidentally, the actual space volume of the reactor can be calculated from the volume of water required to fill the reactor. The actual space volume thereof can be calculated in substantially the same manner in the case where the reactor is charged with a filler.

As for the filler, beads, Raschig ring, Pall ring, Berl saddle, interlock saddle, Tellerette, Hedgehog, HI REX, Cascade mini ring, impulse packing, Sulzer packing, Heli-Pak and the like can be cited. With regard to the materials thereof, fillers that are magnetic, made of a metal, and made of a plastic can be cited and can be chose as appropriate. From the viewpoint of heat conduction, a filler made of a metal is preferably used.

The compound having an N,N-bis(2-hydroxy-3-chloropropyl)amino group obtained in this manner is dehydrochlorinated with alkali to undergo a cyclization reaction so that the compound is converted into a polyfunctional glycidylamine type epoxy compound. In some cases, a step of producing the compound having an N,N-bis(2-hydroxy-3-chloropropyl)amino group is referred to as "addition reaction step" and a step of producing a polyfunctional glycidylamine type epoxy compound from the compound having an N,N-bis(2-hydroxy-3-chloropropyl)amino group as "cyclization reaction step."

As the alkali used in the cyclization reaction step, for example, lithium hydroxide, sodium hydroxide, potassium hydroxide, barium hydroxide, magnesium hydroxide, calcium hydroxide, lithium carbonate, sodium carbonate, potassium carbonate, barium carbonate, magnesium carbonate, calcium carbonate, lithium hydrogen carbonate, sodium hydrogen carbonate, potassium hydrogen carbonate, lithium hydride, sodium hydride, potassium hydride, sodium methoxide, potassium methoxide, sodium ethoxide, potassium ethoxide, sodium n-propoxide, potassium n-propoxide, sodium isopropoxide, potassium isopropoxide, sodium n-butoxide, potassium n-butoxide, sodium tert-butoxide, potassium tert-butoxide, sodium tert-amylate, potassium tert-amylate, sodium n-hexylate, potassium n-hexylate, tetramethyl ammonium hydroxide and the like are mentioned as examples. In particular, sodium hydroxide and potassium hydroxide are preferably used. These alkalis can be used alone or in a combination of two or more species.

Furthermore, the alkali may be put into the solution obtained through the addition reaction, or may also be dissolved in water or an organic solvent and dropped as such a solution.

The amount of the alkali used is preferably 1 to 15 times, by mole, the amount of the amine compound.

It is preferable that the cyclization reaction be conducted in coexistence with a quarternary ammonium salt and/or a quarternary phosphonium salt. By having these salts added and coexisting, the reaction is accelerated and the yield of the polyfunctional glycidylamine based epoxy compound improves.

As the quarternary ammonium salt, bromide salts, chloride salts, iodide salts, hydrogen sulfate salts, hydroxides and the like of tetramethyl ammonium, trimethyl-ethyl ammonium, dimethyl diethyl ammonium, triethyl-methyl ammonium, tripropyl-methyl ammonium, tributyl-methyl ammonium, trioctyl-methyl ammonium, tetraethyl ammonium, trimethyl-propyl ammonium, trimethylphenyl ammonium, benzyl trimethyl ammonium, benzyl triethyl ammonium, diallyl dimethyl ammonium, n-octyl trimethyl ammonium, stearyl trimethyl ammonium, cetyldimethyl ethyl ammonium, tetrapropyl ammonium, tetra-n-butyl ammonium, β-methyl choline, phenyl trimethyl ammonium and the like can be cited. Particularly preferable are the bromide salts, the chloride salts, the hydrogen sulfate salts, and hydroxides of trioctylmethyl ammonium, tetraethyl ammonium, benzyl trimethyl ammonium, benzyl triethyl ammonium, and tetra-n-butyl ammonium.

Furthermore, as the quarternary phosphonium salt, bromide salts, chloride salts, iodide salts, hydrogen sulfate salts, hydroxides and the like of tetramethyl phosphonium, trimethyl-ethyl phosphonium, dimethyl diethyl phosphonium, triethyl-methyl phosphonium, tripropyl-methyl phosphonium, tributyl-methyl phosphonium, trioctyl-methyl phosphonium, tetraethyl phosphonium, trimethyl-propyl phosphonium, trimethylphenyl phosphonium, benzyl trimethyl phosphonium, diallyl dimethyl phosphonium, n-octyl trimethyl phosphonium, stearyl trimethyl phosphonium, cetyldimethyl ethyl phosphonium, tetrapropyl phosphonium, tetra-n-butyl phosphonium, phenyl trimethyl phosphonium, methyl triphenyl phosphonium, ethyl triphenyl phosphonium, tetraphenyl phosphonium and the like can be cited.

The amount of the quarternary ammonium salt added and/or the quarternary phosphonium salt added may be a catalyst quantity and is preferably 0.001 to 0.5 time by mole relative to the amount of the amine compound.

In the cyclization reaction step, the reaction temperature is preferably 0 to 90° C. and more preferably 10 to 70° C. Furthermore, the reaction time is preferably 0.5 to 10 hours after the addition of the alkali compound ends.

In the cyclization reaction step, the alkali, the quarternary ammonium salt and/or the quarternary phosphonium salt may be simply added to or can also be used with a newly added solvent in the solution obtained in the addition reaction step. As the solvent added in the cyclization reaction step, an alcohol based solvent, a hydrocarbon based solvent, an ether based solvent, and an ester based solvent are preferably used.

As the alcohol based solvent, for example, primary alcohols such as methanol, ethanol, 1-propanol, 1-butanol, 1-pentanol, and 1-hexanol, secondary alcohols such as isopropanol, 2-butanol, 2-pentanol, 3-pentanol, 2-hexanol, cyclohexanol, 2-heptanol, and 3-heptanol, tert-butanol, tert-pentanol, ethylene glycol, ethylene glycol monomethyl ether, ethylene glycol monoethyl ether, ethylene glycol mono-n-propyl ether, ethylene glycol mono-n-butyl ether, ethylene glycol monophenyl ether, diethylene glycol, diethylene glycol monomethyl ether, diethylene glycol monoethyl ether, diethylene glycol mono-n-propyl ether, diethylene glycol mono-n-butyl ether, triethylene glycol, triethylene glycol monomethyl ether, triethylene glycol mono-n-butyl ether, propylene glycol, propylene glycol monomethyl ether, propylene glycol monoethyl ether, propylene glycol mono-n-propyl ether, propylene glycol mono-n-butyl ether, propylene glycol monophenyl ether, dipropylene glycol, dipropylene glycol monomethyl ether, dipropylene glycol monoethyl ether, dipropylene glycol mono-n-propyl ether, dipropylene glycol mono-n-butyl ether, tripropylene glycol, tripropylene glycol monomethyl ether, and tripropylene glycol mono-n-butyl ether can be cited.

As the hydrocarbon based solvent, for example, hexane, 2-methyl pentane, 2,2-dimethylbutane, 2,3-dimethylbutane, heptane, octane, isooctane, nonane, trimethyl hexane, decane, dodecane, benzene, toluene, xylene, ethyl benzene, cumene, mesitylene, cyclohexyl benzene, diethyl benzene, cyclopentane, methyl cyclopentane, cyclohexane, methyl cyclohexane, ethyl cyclohexane and the like can be cited.

As the ether based solvent, for example, diisopropyl ether, dibutyl ether, dihexyl ether, anisole, phenetole, diphenyl ether, tetrahydrofuran, tetrahydropyran, ethylene glycol dibutyl ether, diethylene glycol dimethyl ether, diethylene glycol diethyl ether, diethylene glycol dibutyl ether and the like can be cited.

Furthermore, as the ester based solvent, for example, methyl acetate, ethyl acetate, acetic acid propyl, acetic acid isopropyl, butyl acetate, acetic acid isobutyl and the like can be cited.

In particular, solvents that are preferably used are methanol, ethanol, 1-propanol, 1-butanol, isopropanol, 2-butanol, tert-butanol, cyclohexane, toluene, xylene, ethyl benzene, cumene, mesitylene, and diethyl benzene.

The amount of the solvent used in the cyclization reaction step is preferably 0.1 to 20 times by weight the amount of the amine compound and more preferably 1 to 10 times by weight.

Isolation of a polyfunctional glycidylamine type epoxy compound can be achieved by a combination of common unit operations such as (1) removal of an unreacted raw material, (2) removal of a reaction solvent by evaporation, (3) extraction with a hydrophobic solvent, (4) removal of the extraction solvent by evaporation, (5) distillation, and (6) crystallization.

For example, an organic solvent such as toluene is added to a post-cyclization reaction liquid to extract the polyfunctional glycidylamine type epoxy compound into an oil layer and a water layer is separated and removed. Furthermore, it is preferable that the obtained oil layer be washed with water so that salts dissolved in the oil layer are thoroughly removed. The amount of the organic solvent used is preferably 0.2 to 50 times by weight the amount of the object substance and more preferably 1 to 20 times by weight.

Through removal by evaporation of low-boiling point components such as the extraction solvent, unreacted epichlorohydrin or the like from the oil layer, a polyfunctional glycidylamine type epoxy compound is obtained. At the time of removal of the low-boiling point components by evaporation, a thin film distillation apparatus may be used. As the thin film distillation apparatus, a centrifugal molecular distillation apparatus, a falling film type molecular distillation apparatus and the like can be cited. The extraction solvent, the unreacted epichlorohydrin or the like evaporatively removed may be reused.

A polyfunctional glycidylamine type epoxy compound manufactured by using the compound having a N,N-bis(2-hydroxy-3-chloropropyl)amino group obtained through the manufacturing method has a chemical purity greater than or equal to 80% and preferably greater than or equal to 90. If the chemical purity of the polyfunctional glycidylamine type epoxy compound is less than 80%, storage stability becomes low and, in some cases, a resin hardened material hardened by a hardening agent does not have a desired physical property. In this description, the chemical purity of the polyfunctional glycidylamine type epoxy compound is the fraction (HPLC area %) of a peak area of the polyfunctional glycidylamine type epoxy compound measured by a method described later through the use of high-speed liquid chromatography.

EXAMPLES

Concrete descriptions will be given with examples hereinafter and our methods are not restricted only by the examples. Incidentally, analysis values regarding the N,N-bis(2-hydroxy-3-chloropropyl)amine compound and the polyfunctional glycidylamine type epoxy compound obtained in the description were measured by the following methods.

Chemical Purity

By liquid chromatography (CLASS-VP made by Shimadzu Corporation) under the following condition, fractions (HPLC area %) of peak areas of an N,N-bis(2-hydroxy-3-chloropropyl)amine compound and a polyfunctional glycidylamine type epoxy compound were measured and determined as a chemical purity.

Column: YMC-Pack ODS-AM303 4.6φ×250 mm
Column temperature: 40° C.
Mobile phase: a mixed liquid of a composition (A) constituted by a 0.1% (v/v) phosphoric acid aqueous solution and a composition (B) constituted by methanol with a volume ratio (A):(B)=40:60 was used as a mobile phase.
Flow: 1 ml/min
Amount of injection: 3 μl
Detection: UV 254 nm
Analysis time: 80 min
Analysis sample preparation: 0.02 g of a sample was weighed out and diluted in approximately 50 ml of methanol.

However, conditions are not limited to these analysis conditions, provided that the same results as the analysis results based on the foregoing analysis conditions are obtained.

In the following Examples and Comparative Examples, the term "◯◯ time(s) by weight/amine compound" means that the amount of a substance concerned added is ◯◯ times by weight the weight of the amine compound. Furthermore, the term "◯◯ time(s) by mole/amine compound" means that the amount of a substance concerned added is ◯◯ time(s) by mole the molar amount of the amine compound.

Example 1

Addition Reaction:
Using the apparatus illustrated in the FIGURE, a 25 wt % (4-phenoxy aniline)/epichlorohy-drin solution (4-phenoxy aniline:epichlorohydrin =1:6 (molar ratio)) as a reaction raw material liquid and a 11 wt % (iron chloride (III))/isopropanol solution as an acidic compound solution were delivered by liquid delivery pumps at supply velocities of 1.10 g/min and 0.14 g/min, respectively, to a ⅝ inch tubular reactor made of SUS304 (inside diameter: 13.4 mm, length: 400 mm, space volume: 22 ml (charged with φ3 mm alumina balls)) installed within a constant temperature tank at 60° C. (the in-reactor-tube liquid space velocity of the reaction liquid at this time was 3.0 h$^{-1}$). The amount of iron chloride (III) supplied was 0.06 time by mole relative to the amount of the amine compound supplied to the tubular reactor. 150 g of an addition reaction liquid coming out of the reactor exit was acquired. The purity analysis of 4-phenoxy-N,N-bis(2-hydroxy-3-chloropropyl)aniline in the reaction liquid obtained was performed to find that the purity was 96.0% (HPLC area %).

Cyclization Reaction:

1:8 g of tetra-n-butyl ammonium hydrogen sulfate (0.03 time by mole/4-phenoxy aniline) and 97.6 g of a 22% sodium hydroxide aqueous solution (3.0 times by mole/4-phenoxy aniline) were added to the reaction liquid obtained as described above and stirred at a reaction temperature of 30° C. for 2 hours, causing a cyclization react.

After the cyclization reaction ended, standing liquid separation was carried out. 50 g of water and 66 g of toluene were added to the acquired organic layer to perform washing, and then standing liquid separation was carried out. From the acquired organic layer, epichlorohydrin was removed in reduced pressure to obtained 52.8 g of 4-phenoxy-N,N-diglycidyl aniline (weight yield (with reference to 4-phenoxy aniline): 98%). The chemical purity of 4-phenoxy-N,N-diglycidyl aniline obtained was 90.8% (HPLC area %).

Example 2

Addition Reaction:

The addition reaction was performed in substantially in the same manner as in Example 1, except that, unlike Example 1, instead of the 11 wt % (iron chloride (III))/isopropanol solution, acetic acid was delivered as an acidic compound solution at 0.13 g/min to a ⅝ inch tubular reactor made of SUS304 (inside diameter: 13.4 mm, length: 600 mm, space volume: 33 ml (charged with φ3 mm alumina balls)) set at 80° C. within a constant temperature tank. The in-reactor-tube liquid space velocity of the reaction liquid at this time was 2.0 h$^{-1}$. The amount of acetic acid supplied was 1.5 times by mole relative to the amount of the amine compound supplied to the tubular reactor. The purity analysis of 4-phenoxy-N,N-bis(2-hydroxy-3-chloropropyl)aniline in the reaction liquid obtained was performed to find that the purity was 95.5% (HPLC area %).

Cyclization Reaction:

The cyclization reaction was conducted in substantially the same manner as in Example 1, except that 164 g of a 22% sodium hydroxide aqueous solution (5.0 times by mole/4-phenoxy aniline) was added to the reaction liquid obtained by the foregoing addition reaction.

By this cyclization reaction, 52.3 g of 4-phenoxy-N,N-diglycidyl aniline (weight yield (with reference to 4-phenoxy aniline): 97%) was obtained. The chemical purity of 4-phenoxy-N,N-diglycidyl aniline obtained was 93.7% (HPLC area %).

Example 3

Addition Reaction:

The addition reaction was performed in substantially the same manner as in Example 2, except that, unlike Example 2, a ⅝ inch tubular reactor made of SUS304 (inside diameter: 13.4 mm, length: 400 mm, a space volume of 48 ml (made by Sibata Scientific Technology Ltd., made of SUS316L, charged with Helipack No. 1). The in-reactor-tube liquid space velocity of the reaction liquid at this time was 1.4 h$^{-1}$. The purity analysis of 4-phenoxy-N,N-bis(2-hydroxy-3-chloropropyl)aniline in the reaction liquid obtained was performed to find that the purity was 96.5% (HPLC area %).

Cyclization Reaction:

Using the reaction liquid obtained by the foregoing addition reaction, the cyclization reaction was conducted in substantially the same manner as in Example 2.

By this cyclization reaction, 53.9 g of 4-phenoxy-N,N-diglycidyl aniline (weight yield (with reference to 4-phenoxy aniline): 100%) was obtained. The chemical purity of 4-phenoxy-N,N-diglycidyl aniline obtained was 94.9% (HPLC area %).

Example 4

Addition Reaction:

The addition reaction was performed in substantially the same manner as in Example 2, except that, unlike Example 2, a ⅝ inch tubular reactor made of SUS304 (inside diameter: 13.4 mm, length: 1000 mm, a space volume of 120 ml (made by Sibata Scientific Technology Ltd., made of SUS316L, charged with Helipack No. 1)) was used. The in-reactor-tube liquid space velocity of the reaction liquid at this time was 0.5 h$^{-1}$. The purity analysis of 4-phenoxy-N,N-bis(2-hydroxy-3-chloropropyl)aniline in the reaction liquid obtained was performed to find that the purity was 92.6% (HPLC area %).

Cyclization Reaction:

Using the reaction liquid obtained by the foregoing addition reaction, the cyclization reaction was conducted in substantially the same manner as in Example 2.

By this cyclization reaction, 52.3 g of 4-phenoxy-N,N-diglycidyl aniline (weight yield (with reference to 4-phenoxy aniline): 97%) was obtained. The chemical purity of 4-phenoxy-N,N-diglycidyl aniline obtained was 82.2% (HPLC area %).

Example 5

Addition Reaction:

The addition reaction was performed in substantially the same manner as in Example 2, except that, unlike Example 2, a 16.6 wt % (4-phenoxy aniline)/(epichlorohydrin+toluene)solution (4-phenoxy aniline:epichlorohydrin=1:6 (molar ratio)) was delivered as a reaction raw material liquid at a supply velocity of 1.65 g/min and a ⅝ inch tubular reactor made of SUS304 (inside diameter: 13.4 mm, length: 600 mm, a space volume of 72 ml (made by Sibata Scientific Technology Ltd., made of SUS316L, charged with Helipack No. 1)) was used. The in-reactor-tube liquid space velocity of the reaction liquid at this time was 1.4 h$^{-1}$. The purity analysis of 4-phenoxy-N,N-bis(2-hydroxy-3-chloropropyl) aniline in the reaction liquid obtained was performed to find that the purity was 95.9% (HPLC area %).

Cyclization Reaction:

Using the reaction liquid obtained by the foregoing addition reaction, the cyclization reaction was conducted in substantially the same manner as in Example 2.

By this cyclization reaction, 52.6 g of 4-phenoxy-N,N-diglycidyl aniline (weight yield (with reference to 4-phenoxy aniline): 98%) was obtained. The chemical purity of 4-phenoxy-N,N-diglycidyl aniline obtained was 94.8% (HPLC area %).

Comparative Example 1

Addition Reaction:

The addition reaction was performed in substantially the same manner as in Example 2, except that, unlike Example 2, a ⅝ inch tubular reactor made of SUS304 (inside diameter: 13.4 mm, length: 200 mm, a space volume of 24 ml (made by Sibata Scientific Technology Ltd., made of SUS316L, charged with Helipack No. 1)) was used and, as reaction raw material liquids, a 25 wt % (4-phenoxy aniline)/epichlorohydrin solution (4-phenoxy aniline:epichlorohydrin=1:6 (molar ratio)) was supplied at a supply velocity of 8.0 g/min and acetic acid at 0.95 g/min. The in-reactor-tube liquid space velocity of the reaction liquid at this time was 20 h$^{-1}$. The amount of acetic acid supplied was 1.5 times by mole relative to the amount of the amine compound supplied to the flow reactor. The purity analysis of 4-phenoxy-N,N-bis(2-hydroxy-3-chloropropyl)aniline in the reaction liquid obtained was performed to find that the purity was 41.6% (HPLC area %).

Cyclization Reaction:

Using the reaction liquid obtained by the foregoing addition reaction, the cyclization reaction was conducted in substantially the same manner as in Example 2.

The chemical purity of 4-phenoxy-N,N-diglycidyl aniline obtained was 35.2% (HPLC area %).

Comparative Example 2

Addition Reaction:

The addition reaction was performed in substantially the same manner as in Example 2, except that, unlike Example 2, a ⅝ inch tubular reactor made of SUS304 (inside diameter: 13.4 mm, length: 1000 mm, a space volume of 120 ml (made by Sibata Scientific Technology Ltd., made of SUS316L, charged with Helipack No. 1)) was used and, as reaction raw material liquids, a 25 wt % (4-phenoxy aniline)/epichlorohydrin solution (4-phenoxy aniline:epichlorohydrin=1:6 (molar ratio)) was supplied at a supply velocity of 0.22 g/min and acetic acid at 0.026 g/min. The in-reactor-tube liquid space velocity of the reaction liquid at this time was 0.1 h$^{-1}$. The amount of acetic acid supplied was 1.5 times by mole relative to the amount of the amine compound supplied to the flow reactor. The purity analysis of 4-phenoxy-N,N-bis(2-hydroxy-3-chloropropyl)aniline in the reaction liquid obtained was performed to find that the purity was 78.3% (HPLC area %).

Cyclization Reaction:

Using the reaction liquid obtained by the foregoing addition reaction, the cyclization reaction was conducted in substantially the same manner as in Example 2.

By this cyclization reaction, 46.0 g of 4-phenoxy-N,N-diglycidyl aniline (weight yield (with reference to 4-phenoxy aniline): 85%) was obtained. The chemical purity of 4-phenoxy-N,N-diglycidyl aniline obtained was 79.2% (HPLC area %).

Comparative Example 3

Addition Reaction:

The addition reaction was performed in substantially the same manner as in Example 2, except that, unlike Example 2, no acidic compound was supplied. The in-reactor-tube liquid space velocity of the reaction liquid at this time was 2.0 h$^{-1}$. The purity analysis of 4-phenoxy-N,N-bis(2-hydroxy-3-chloropropyl)aniline in the reaction liquid obtained was performed to find that the purity was 30.2% (HPLC area %).

Cyclization Reaction:

Using the reaction liquid obtained by the foregoing addition reaction, the cyclization reaction was conducted in substantially the same manner as in Example 2.

The chemical purity of 4-phenoxy-N,N-diglycidyl aniline obtained was 24.5% (HPLC area %).

Comparative Example 4

Addition Reaction:

The addition reaction was performed in substantially the same manner as in Example 2, except that, instead of the acidic compound in Example 2, water was supplied at 0.04 g/min. The in-reactor-tube liquid space velocity of the reaction liquid at this time was 1.4 h$^{-1}$. Incidentally, the amount of water supplied was 1.5 times by mole relative to the amount of the amine compound supplied to the tubular reactor. The purity analysis of 4-phenoxy-N,N-bis(2-hydroxy-3-chloropropyl)aniline in the reaction liquid obtained was performed to find that the purity was 23.0% (HPLC area %).

Cyclization Reaction:

Using the reaction liquid obtained by the foregoing addition reaction, the cyclization reaction was conducted in substantially the same manner as in Example 2.

The chemical purity of 4-phenoxy-N,N-diglycidyl aniline obtained was 20.0% (HPLC area %).

Example 6

Addition Reaction:

Using the apparatus illustrated in the FIGURE, a 15.3 wt % (3,4'-diaminodiphenyl ether)/epichlorohydrin solution (3,4'-diaminodiphenyl ether:epichlorohydrin=1:12 (molar ratio)) as a reaction raw material liquid and acetic acid as an acidic compound solution were delivered by liquid delivery pumps at supply velocities of 1.16 g/min and 0.08 g/min, respectively, to a ⅝ inch tubular reactor made of SUS304 (inside diameter: 13.4 mm, length: 800 mm, space volume: 96 ml (made by Sibata Scientific Technology Ltd., made of SUS316L, charged with Helipack No. 1)) installed within a constant temperature tank at 80° C. (the in -reactor-tube liquid space velocity of the reaction liquid at this time was 0.7 h$^{-1}$). Incidentally, the amount of acetic acid supplied was 1.5 times by mole relative to the amount of the amine compound supplied to the tubular reactor. 200 g of an addition reaction liquid coming out of the reactor exit was acquired. The purity analysis of N,N,N',N'-tetrakis(2-hydroxy-3-chloropropyl)3,4'-diaminodiphenyl ether in the reaction liquid obtained was performed to find that the purity was 93.5% (HPLC area %).

Cyclization Reaction:

1.45 g of tetra-n-butyl ammonium hydrogen sulfate (0.03 time by mole/3,4'-diaminodiphenyl ether) and 181.7 g of a 22% sodium hydroxide aqueous solution (7.0 times by mole/3,4'-diaminodiphenyl ether) were added to the reaction liquid obtained as described above and stirred at a reaction temperature of 30° C. for 2 hours, causing a cyclization reaction.

After the cyclization reaction ended, standing liquid separation was carried out. 85.8 g of water was added to the acquired organic layer to perform washing, and then standing liquid separation was carried out. From the acquired organic layer, epichlorohydrin was removed in reduced pressure to obtain 57.3 g of N,N,N',N'-tetraglycidyl 3,4'-diaminodiphenyl ether (weight yield (with reference to 3,4'-diaminodiphenyl ether): 94.6%). The chemical purity of N,N,N',N'-tetraglycidyl 3,4'-diaminodiphenyl ether obtained was 91.8% (HPLC area %).

Example 7

Addition Reaction:
The addition reaction was performed in substantially the same manner as in Example 6, except that, unlike Example 6, lactic acid was supplied as an acidic compound at 0.12 g/min. Incidentally, the amount of lactic acid supplied was 1.5 times by mole relative to the amount of the amine compound supplied to the tubular reactor. The in-reactor-tube liquid space velocity of the reaction liquid at this time was 0.7 h$^{-1}$. The purity analysis of N,N,N',N'-tetrakis(2-hydroxy-3-chloropropyl)3,4'-diaminodiphenyl ether in the reaction liquid obtained was performed to find that the purity was 93.0% (HPLC area %).
Cyclization Reaction:
Using the reaction liquid obtained by the foregoing addition reaction, the cyclization reaction was conducted in substantially the same manner as in Example 6.
By this cyclization reaction, 56.2 g of N,N,N',N'-tetraglycidyl 3,4'-diaminodiphenyl ether (weight yield (with reference to 3,4'-diaminodiphenyl ether): 95.8%) was obtained. The chemical purity of N,N,N',N'-tetraglycidyl 3,4'-diaminodiphenyl ether obtained was 86.7% (HPLC area %).

Comparative Example 5

Addition Reaction:
The addition reaction was performed in substantially the same manner as in Example 6, except that, unlike Example 6, the supply velocity of acetic acid to a ⅝ inch tubular reactor made of SUS304 (inside diameter: 13.4 mm, length: 200 mm, space volume: 24 ml (made by Sibata Scientific Technology Ltd., made of SUS316L, charged with Helipack No. 1)) was 0.57 g/min and 3,4'-diaminodiphenyl ether/epichlorohydrin solution (3,4'-diaminodiphenyl ether:epichlorohydrin=1:12 (molar ratio)) was supplied thereto at 8.32 g/min. The in-reactor-tube liquid space velocity of the reaction liquid at this time was 20.0 h$^{-1}$. The purity analysis of N,N,N',N'-tetrakis(2-hydroxy-3-chloropropyl)3,4'-diaminodiphenyl ether in the reaction liquid obtained was performed to find that the purity was 30.3% (HPLC area %).
Cyclization Reaction:
Using the reaction liquid obtained by the foregoing addition reaction, the cyclization reaction was conducted in substantially the same manner as in Example 6.
The chemical purity of N,N,N',N'-tetraglycidyl 3,4'-diaminodiphenyl ether obtained was 41.7% (HPLC area %).

Comparative Example 6

Addition Reaction:
The addition reaction was performed in substantially the same manner as in Example 6, except that, unlike Example 6, acetic acid was supplied to a ⅝ inch tubular reactor made of SUS304 (inside diameter: 13.4 mm, length: 800 mm, space volume: 96 ml (made by Sibata Scientific Technology Ltd., made of SUS316L, charged with Helipack No. 1)) at 0.012 g/min and 3,4'-diaminodiphenyl ether/epichlorohydrin solution (3,4'-diaminodiphenyl ether:epichlorohydrin=1:12 (molar ratio)) at 0.174 g/min. The in-reactor-tube liquid space velocity of the reaction liquid at this time was 0.1 h$^{-1}$. The purity analysis of N,N,N',N'-tetrakis(2-hydroxy-3-chloropropyl)3,4'-diaminodiphenyl ether in the reaction liquid obtained was performed to find that the purity was 52.3% (HPLC area %).
Cyclization Reaction:
Using the reaction liquid obtained by the foregoing addition reaction, the cyclization reaction was conducted in substantially the same manner as in Example 6.
By this cyclization reaction, 59.8 g of N,N,N',N'-tetraglycidyl 3,4'-diaminodiphenyl ether (weight yield (with reference to 3,4'-diaminodiphenyl ether): 97.7%) was obtained. The chemical purity of N,N,N',N'-tetraglycidyl 3,4'-diaminodiphenyl ether obtained was 63.3% (HPLC area %).

Comparative Example 7

Addition Reaction:
The addition reaction was performed in substantially the same manner as in Example 6, except that, unlike Example 6, the reaction temperature was 30° C. The purity analysis of N,N,N',N'-tetrakis(2-hydroxy-3-chloropropyl)3,4'-diaminodiphenyl ether in the reaction liquid obtained was performed to find that the purity was 7.0% (HPLC area %).
Cyclization Reaction:
Using the reaction liquid obtained by the foregoing addition reaction, the cyclization reaction was conducted in substantially the same manner as in Example 6.
The chemical purity of N,N,N',N'-tetraglycidyl 3,4'-diaminodiphenyl ether obtained was 27.5% (HPLC area %).

Comparative Example 8

Addition Reaction:
The addition reaction was performed in substantially the same manner as in Example 6, except that, unlike Example 6, no acidic compound was used. The purity analysis of N,N,N',N'-tetrakis(2-hydroxy-3-chloropropyl)3,4'-diaminodiphenyl ether in the obtained reaction liquid was performed but production of N,N,N',N'-tetrakis(2-hydroxy-3-chloropropyl)3,4'-diaminodiphenyl ether was not recognized. Therefore, the cyclization reaction was not performed.

Example 8

Addition Reaction:
Using the apparatus illustrated in the FIGURE, 11.6 wt % (m-amino phenol)/epichlorohydrin solution (m-amino phenol:epichlorohydrin=1:9 (molar ratio)) as a reaction raw material liquid and acetic acid as an acidic compound solution were delivered by liquid delivery pumps at supply velocities of 1.13 g/min and 0.11 g/min, respectively, to a ⅝ inch tubular reactor made of SUS304 (inside diameter: 13.4 mm, length: 400 mm, space volume: 48 ml (made by Sibata Scientific Technology Ltd., made of SUS316L, charged with Helipack No. 1)) installed within a constant temperature tank at 70° C. (the in-reactor-tube liquid space velocity of the reaction liquid at this time was 1.4 h$^{-1}$). The amount of acetic acid supplied was 1.5 times by mole relative to the amount of the amine compound supplied to the tubular reactor. 200 g of an addition reaction liquid coming out of the reactor exit was acquired. The purity analysis of N,N-bis(2-hydroxy-3-chloropropyl)-m-amino phenol in the reaction liquid obtained was performed to find that the purity was 98.1% (HPLC area %).

Cyclization Reaction:

52.9 g of isopropyl alcohol (4.5 times by mole/m-amino phenol) and 186.8 g of a 22% sodium hydroxide aqueous solution (5.3 times by mole/m-amino phenol) were added to the reaction liquid obtained as described above and stirred at a reaction temperature of 40° C. for 2 hours, causing a cyclization reaction.

After the cyclization reaction ended, standing liquid separation was performed. 63.5 g of water was added to the acquired organic layer to perform washing, and then standing liquid separation was performed. From the acquired organic layer, epichlorohydrin was removed in reduced pressure to obtain 45.3 g of triglycidyl-m-amino phenol (weight yield (with reference to m-amino phenol): 84.0%). The chemical purity of triglycidyl-m-amino phenol obtained was 72.0% (HPLC area %).

Comparative Example 9

Addition Reaction:

The addition reaction was performed in substantially the same manner as in Example 8, except that, unlike Example 8, the supply velocity of acetic acid to a ⅝ inch tubular reactor made of SUS304 (inside diameter: 13.4 mm, length: 200 mm, space volume: 24 ml (made by Sibata Scientific Technology Ltd., made of SUS316L, charged with Helipack No. 1)) was 0.78 g/min and m-amino phenol/epichlorohydrin solution (m-amino phenol:epichlorohydrin=1:9 (molar ratio)) was supplied thereto at 8.11 g/min. The in-reactor-tube liquid space velocity of the reaction liquid at this time was 20.0 h$^{-1}$. The purity analysis of N,N-bis(2-hydroxy-3-chloropropyl)-m-amino phenol in the reaction liquid obtained was performed to find that the purity was 59.4% (HPLC area %).

Cyclization Reaction:

Using the reaction liquid obtained by the foregoing addition reaction, the cyclization reaction was conducted in substantially the same manner as in Example 8, except that the reaction temperature was 30° C. and, as a phase transfer catalyst, 1.97 g of tetra-n-butyl ammonium hydrogen sulfate (0.03 time by mole/m-amino phenol) was used.

By this cyclization reaction, 37.2 g of triglycidyl-m-amino phenol (weight yield (with reference to m-amino phenol): 69.4%) was obtained. The chemical purity of triglycidyl-m-amino phenol obtained was 48.4% (HPLC area %).

Comparative Example 10

Addition Reaction:

The addition reaction was performed in substantially the same manner as in Example 6, except that, unlike Example 8, acetic acid was supplied at 0.016 g/min to a ⅝ inch tubular reactor made of SUS304 (inside diameter: 13.4 mm, length: 800 mm, space volume: 96 ml (made by Sibata Scientific Technology Ltd., made of SUS316L, charged with Helipack No. 1)) and an m-amino phenol/epichlorohydrin solution (m-amino phenol:epichlorohydrin=1:9 (molar ratio)) at 0.170 g/min. The in-reactor-tube liquid space velocity of the reaction liquid at this time was 0.1 h$^{-1}$. The purity analysis of N,N-bis(2-hydroxy-3-chloropropyl)-m-amino phenol in the reaction liquid obtained was performed to find that the purity was 77.7% (HPLC area %).

Cyclization Reaction:

Using the reaction liquid obtained by the foregoing addition reaction, the cyclization reaction was conducted in substantially the same manner as in Comparative Example 9.

By this cyclization reaction, 32.6 g of triglycidyl-m-amino phenol (weight yield (with reference to m-amino phenol): 60.7%) was obtained. The chemical purity of triglycidyl-m-amino phenol obtained was 39.8% (HPLC area %).

Comparative Example 11

Addition Reaction:

The addition reaction was performed in substantially the same manner as in Example 8, except that, unlike Example 8, the reaction temperature was 30° C. The purity analysis of N,N-bis(2-hydroxy-3-chloropropyl)-m-amino phenol in the reaction liquid obtained was performed to find that the purity was 87.1% (HPLC area %).

Cyclization Reaction:

Using the reaction liquid obtained by the foregoing addition reaction, the cyclization reaction was conducted in substantially the same manner as in Comparative Example 9.

By this cyclization reaction, 35.3 g of triglycidyl-m-amino phenol (weight yield (with reference to m-amino phenol): 65.7%) was obtained. The chemical purity of triglycidyl-m-amino phenol obtained was 46.3% (HPLC area %).

Comparative Example 12

Addition Reaction:

The addition reaction was performed in substantially the same manner as in Example 8, except that, unlike Example 8, no acidic compound was supplied. The in-reactor-tube liquid space velocity of the reaction liquid at this time was 1.4 h$^{-1}$. The purity analysis of N,N-bis(2-hydroxy-3-chloropropyl)-m-amino phenol in the reaction liquid obtained was performed to find that the purity was 74.8% (HPLC area %).

Cyclization Reaction:

Using the reaction liquid obtained by the foregoing addition reaction, the cyclization reaction was conducted in substantially the same manner as in Comparative Example 9.

By this cyclization reaction, 38.2 g of triglycidyl-m-amino phenol (weight yield (with reference to m-amino phenol): 71.1%) was obtained. The chemical purity of triglycidyl-m-amino phenol obtained was 58.2% (HPLC area %).

Example 9

Addition Reaction:

Using the apparatus illustrated in the FIGURE, a 15.2 wt % (4,4'-diaminodiphenyl methane)/epichlorohydrin solution (4,4'-diaminodiphenyl methane:epichlorohydrin =1:12 (molar ratio)) as a reaction raw material liquid and acetic acid as an acidic compound solution were delivered by liquid delivery pumps at supply velocities of 1.16 g/min and 0.08 g/min, respectively, to a ⅝ inch tubular reactor made of SUS304 (inside diameter: 13.4 mm, length: 400 mm, space volume: 48 ml (made by Sibata Scientific Technology Ltd., made of SUS316L, charged with Helipack No.1)) installed within a constant temperature tank at 80° C. (the in-reactor-tube liquid space velocity of the reaction liquid at this time was 1.4 h$^{-1}$). The amount of acetic acid supplied was 1.5 times by mole relative to the amount of the amine compound supplied to the tubular reactor. 200 g of an addition reaction liquid coming out of the reactor exit was acquired. The purity analysis of N,N,N',N'-tetrakis(2-hydroxy-3-chloropropyl)4,4'-diaminodiphenyl methane in the reaction liquid obtained was performed to find that the purity was 93.9% (HPLC area %).

Cyclization Reaction:

1.46 g of tetra-n-butyl ammonium hydrogen sulfate (0.03 time by mole/4,4'-diaminodiphenyl methane) and 182.0 g of a 22% sodium hydroxide aqueous solution (7.0 times by mole/4,4'-diaminodiphenyl methane) were added to the reaction liquid obtained as described above and stirred at a reaction temperature of 30° C. for 2 hours, causing a cyclization react.

After the cyclization reaction ended, standing liquid separation was performed. 85.1 g of water was added to the acquired organic layer to perform washing, and then standing liquid separation was performed. From the acquired organic layer, epichlorohydrin was removed in reduced pressure to obtain 53.4 g of N,N,N',N'-tetraglycidyl 4,4'-diaminodiphenyl methane (weight yield (with reference to 4,4'-diaminodiphenyl methane): 88.4%). The chemical purity of N,N,N',N'-tetraglycidyl 4,4'-diaminodiphenyl methane obtained was 90.0% (HPLC area %).

Comparative Example 13

Addition Reaction:

The addition reaction was performed in substantially the same manner as in Example 9, except that, unlike Example 9, the supply velocity of acetic acid to a ⅝ inch tubular reactor made of SUS304 (inside diameter: 13.4 mm, length: 200 mm, space volume: 24 ml (made by Sibata Scientific Technology Ltd., made of SUS316L, charged with Helipack No. 1)) was 0.57 g/min and 4,4'-diaminodiphenyl methane/epichlorohydrin solution (4,4'-diaminodiphenyl methane:epichlorohydrin=1:12 (molar ratio)) was supplied thereto at 8.32 g/min. The in-reactor-tube liquid space velocity of the reaction liquid at this time was 20.0 $h^{-1}$. The purity analysis of N,N,N',N'-tetrakis(2-hydroxy-3-chloropropyl)4,4'-diaminodiphenyl methane in the obtained reaction liquid was performed to find that the purity was 16.8% (HPLC area %).

Cyclization Reaction:

Using the reaction liquid obtained by the foregoing addition reaction, the cyclization reaction was conducted in substantially the same manner as in Example 9.

The chemical purity of N,N,N',N'-tetraglycidyl 4,4'-diaminodiphenyl methane obtained was 25.3% (HPLC area %).

Comparative Example 14

Addition Reaction:

The addition reaction was performed in substantially the same manner as in Example 9, except that, unlike Example 9, acetic acid was supplied at 0.012 g/min to a ⅝ inch tubular reactor made of SUS304 (inside diameter: 13.4 mm, length: 800 mm, space volume: 96 ml (made by Sibata Scientific Technology Ltd., made of SUS316L, charged with Helipack No. 1)) and 4,4'-diaminodiphenyl methane/epichlorohydrin solution (4,4'-diaminodiphenyl methane:epichlorohydrin=1:12 (molar ratio)) at 0.174 g/min. The in-reactor-tube liquid space velocity of the reaction liquid at this time was 0.1 $h^{-1}$. The purity analysis of N,N,N',N'-tetrakis(2-hydroxy-3-chloropropyl)4,4'-diaminodiphenyl methane in the reaction liquid obtained was performed to find that the purity was 51.7% (HPLC area %).

Cyclization Reaction:

Using the reaction liquid obtained by the foregoing addition reaction, the cyclization reaction was conducted in substantially the same manner as in Example 9.

By this cyclization reaction, 60.0 g of N,N,N',N'-tetraglycidyl 4,4'-diaminodiphenyl methane (weight yield (with reference to 4,4'-diaminodiphenyl methane): 100%) was obtained. The chemical purity of N,N,N',N'-tetraglycidyl 4,4'-diaminodiphenyl methane obtained was 56.9% (HPLC area %).

Comparative Example 15

Addition Reaction:

The addition reaction was performed in substantially the same manner as in Example 9, except that, unlike Example 9, the reaction temperature was 30° C. The purity analysis of N,N,N',N'-tetrakis(2-hydroxy-3-chloropropyl)4,4'-diaminodiphenyl methane in the reaction liquid obtained was performed to find that the purity was 18.6% (HPLC area %).

Cyclization Reaction:

Using the reaction liquid obtained by the foregoing addition reaction, the cyclization reaction was conducted in substantially the same manner as in Example 9.

By this cyclization reaction, 51.8 g of N,N,N',N'-tetraglycidyl 4,4'-diaminodiphenyl methane (weight yield (with reference to 4,4'-diaminodiphenyl methane): 85.8%) was obtained. The chemical purity of N,N,N',N'-tetraglycidyl 4,4'-diaminodiphenyl methane obtained was 54.6% (HPLC area %).

Comparative Example 16

Addition Reaction:

The addition reaction was performed in substantially the same manner as in Example 9, except that, unlike Example 9, no acidic compound was used. The purity analysis of N,N,N',N'-tetrakis(2-hydroxy-3-chloropropyl)4,4'-diaminodiphenyl methane in the obtained reaction liquid was performed but production of N,N,N',N'-tetrakis(2-hydroxy-3-chloropropyl)4,4'-diaminodiphenyl ether was not recognized. Therefore, the cyclization reaction was not performed.

Example 10

Addition Reaction:

Using the apparatus illustrated in the FIGURE, a 14.4 wt % (aniline)/epichlorohydrin solution (aniline:epichlorohydrin=1:6 (molar ratio)) as a reaction raw material liquid and acetic acid as an acidic compound solution were delivered by liquid delivery pumps at supply velocities of 1.09 g/min and 0.15 g/min, respectively, to a ⅝ inch tubular reactor made of SUS304 (inside diameter: 13.4mm, length: 400 mm, space volume: 48 ml (made by Sibata Scientific Technology Ltd., made of SUS316L, charged with Helipack No.1)) installed within a constant temperature tank at 70° C. (the in-reactor-tube liquid space velocity of the reaction liquid at this time was 1.4 $h^{-1}$). The amount of acetic acid supplied was 1.5 times by mole relative to the amount of the amine compound supplied to the tubular reactor. 200 g of an addition reaction liquid coming out of the reactor exit was acquired. The purity analysis of N,N-bis(2-hydroxy-3-chloropropyl)-aniline in the reaction liquid obtained was performed to find that the purity was 98.6% (HPLC area %).

Cyclization Reaction:

2.76 g of tetra-n-butyl ammonium hydrogen sulfate (0.03 time by mole/aniline) and 246.3 g of a 22% sodium hydroxide aqueous solution (5.0 times by mole/aniline) was added to the reaction liquid obtained as described above and stirred at a reaction temperature of 30° C. for 2 hours, causing a cyclization react.

After the cyclization reaction ended, standing liquid separation was performed. 37.8 g of water was added to the acquired organic layer to perform washing, and then standing liquid separation was performed. From the acquired organic layer, epichlorohydrin was removed in reduced pressure to obtain 52.3 g of N,N-diglycidyl aniline (weight yield (with reference to aniline): 93.9%). The chemical purity of N,N-diglycidyl aniline obtained was 96.0% (HPLC area %).

Comparative Example 17

Addition Reaction:

The addition reaction was performed in substantially the same manner as in Example 10, except that, unlike Example 10, the supply velocity of acetic acid to a ⅝ inch tubular reactor made of SUS304 (inside diameter: 13.4 mm, length: 200 mm, space volume: 24 ml (made by Sibata Scientific Technology Ltd., made of SUS316L, charged with Helipack No. 1)) was 1.08 g/min and aniline/epichlorohydrin solution (aniline:epichlorohydrin=1:6 (molar ratio)) was supplied thereto at 7.8 g/min. The in-reactor-tube liquid space velocity of the reaction liquid at this time was 20.0 h$^{-1}$. The purity analysis of N,N-bis(2-hydroxy-3-chloropropyl)-aniline in the reaction liquid obtained was performed to find that the purity was 74.1 (HPLC area %).

Cyclization Reaction:

Using the reaction liquid obtained by the foregoing addition reaction, the cyclization reaction was conducted in substantially the same manner as in Example 10.

By this cyclization reaction, 41.3 g of N,N-diglycidyl aniline (weight yield (with reference to aniline) 74.3%) was obtained. The chemical purity of N,N-diglycidyl aniline obtained was 72.6% (HPLC area %).

Comparative Example 18

Addition Reaction:

The addition reaction was performed in substantially the same manner as in Example 10, except that, unlike Example 10, acetic acid was supplied at 0.023 g/min to a ⅝ inch tubular reactor made of SUS304 (inside diameter: 13.4 mm, length: 800 mm, space volume: 96 ml (made by Sibata Scientific Technology Ltd., made of SUS316L, charged with Helipack No. 1)) and aniline/epichlorohydrin solution (aniline:epichlorohydrin=1:6 (molar ratio)) at 0.163 g/min. The in-reactor-tube liquid space velocity of the reaction liquid at this time was 0.1 h$^{-1}$. The purity analysis of N,N-bis(2-hydroxy-3-chloropropyl)-aniline in the reaction liquid obtained was performed to find that the purity was 86.8% (HPLC area %).

Cyclization Reaction:

Using the reaction liquid obtained by the foregoing addition reaction, the cyclization reaction was conducted in substantially the same manner as in Example 10.

By this cyclization reaction, 54.5 g of N,N-diglycidyl aniline (weight yield (with reference to aniline): 97.9%) was obtained. The chemical purity of N,N-diglycidyl aniline obtained was 89.9% (HPLC area %).

Comparative Example 19

Addition Reaction:

The addition reaction was performed in substantially the same manner as in Example 10, except that, unlike Example 10, the reaction temperature was 30° C. The purity analysis of N,N-bis(2-hydroxy-3-chloropropyl)-aniline in the reaction liquid obtained was performed to find that the purity was 80.7% (HPLC area %).

Cyclization Reaction:

Using the reaction liquid obtained by the foregoing addition reaction, the cyclization reaction was conducted in substantially the same manner as in Example 10.

By this cyclization reaction, 46.1 g of N,N-diglycidyl aniline (weight yield (with reference to aniline): 82.8%) was obtained. The chemical purity of N,N-diglycidyl aniline obtained was 94.1% (HPLC area %).

Comparative Example 20

Addition Reaction:

The addition reaction was performed in substantially the same manner as in Example 10, except that, unlike Example 10, no acidic compound was used. The purity analysis of N,N-bis(2-hydroxy-3-chloropropyl)-aniline in the reaction liquid obtained was performed but production of N,N-bis(2-hydroxy-3-chloropropyl)-aniline was not recognized. Therefore, the cyclization reaction was not performed.

Reaction conditions and evaluation results of Examples 1 to 5 and Comparative Examples 1 to 4 are collectively mentioned in Table 1, reaction conditions and evaluation results of Examples 6 to 7 and Comparative Examples 5 to 8 in Table 2, reaction conditions and evaluation results of Example 8 and Comparative Examples 9 to 12 in Table 3, reaction conditions and evaluation results of Example 9 and Comparative Examples 13 to 16 in Table 4, and reaction conditions and evaluation results of Example 10 and Comparative Examples 17 to 20 in Table 5.

TABLE 1

|  |  |  | Example 1 | Example 2 | Example 3 | Example 4 | Example 5 |
|---|---|---|---|---|---|---|---|
| Addition reaction | Raw material (amine compound) |  | 4-phenoxy aniline | 4-phenoxy aniline | 4-phenoxy aniline | 4-phenoxy Aniline | 4-phenoxy aniline |
|  | Amount of epichlorohydrin | Time(s) by mole*[1] | 6.0 | 6.0 | 6.0 | 6.0 | 6.0 |
|  | Acidic compound |  | FeCl$_3$ | Acetic acid | Acetic acid | Acetic acid | Acetic acid |
|  | Amount of acidic compound | Time(s) by mole*[1] | 0.06 | 1.5 | 1.5 | 1.5 | 1.5 |
|  | Solvent |  | —*[3] | —*[3] | —*[3] | —*[3] | Toluene |
|  | Amount of solvent | Time(s) by weight | — | — | — | — | 2 |
|  | Liquid space velocity | h$^{-1}$ | 3.0 | 2.0 | 1.4 | 0.5 | 1.4 |
|  | Reaction temperature | ° C. | 60 | 80 | 80 | 80 | 80 |
|  | Purity of N,N-bis(2-hydroxy-3-chloropropyl)amine compound | HPLC area % | 96.0 | 95.5 | 96.5 | 92.6 | 95.9 |

TABLE 1-continued

| | | | | | | | |
|---|---|---|---|---|---|---|---|
| Cyclization reaction | Reaction time | Hour | 2 | 2 | 2 | 2 | 2 |
| | Kind of catalyst[*2] | | TBAHS | TBAHS | TBAHS | TBAHS | TBAHS |
| | Amount of catalyst | Time(s) by mole[*1] | 0.03 | 0.03 | 0.03 | 0.03 | 0.03 |
| | Reaction temperature | ° C. | 30 | 30 | 30 | 30 | 30 |
| | Purity of epoxy compound | HPLC area % | 90.8 | 93.7 | 94.9 | 82.2 | 94.8 |
| | Yield of epoxy compound | % | 98.0 | 97.0 | 100.0 | 97.0 | 98.0 |

| | | | Comparative Example 1 | Comparative Example 2 | Comparative Example 3 | Comparative Example 4 |
|---|---|---|---|---|---|---|
| Addition reaction | Raw material (amine compound) | | 4-phenoxy aniline | 4-phenoxy aniline | 4-phenoxy aniline | 4-phenoxy aniline |
| | Amount of epichlorohydrin | Time(s) by mole[*1] | 6.0 | 6.0 | 6.0 | 6.0 |
| | Acidic compound | | Acetic acid | Acetic acid | —[*3] | $H_2O$ |
| | Amount of acidic compound | Time(s) by mole[*1] | 1.5 | 1.5 | — | 1.5 |
| | Solvent | | —[*3] | —[*3] | —[*3] | —[*3] |
| | Amount of solvent | Time(s) by weight | — | — | — | — |
| | Liquid space velocity | $h^{-1}$ | 20.0 | 0.1 | 2.0 | 1.4 |
| | Reaction temperature | ° C. | 80 | 80 | 80 | 80 |
| | Purity of N,N-bis(2-hydroxy-3-chloropropyl)amine compound | HPLC area % | 41.6 | 78.3 | 30.2 | 23.0 |
| Cyclization reaction | Reaction time | Hour | 2 | 2 | 2 | 2 |
| | Kind of catalyst[*2] | | TBAHS | TBAHS | TBAHS | TBAHS |
| | Amount of catalyst | Time(s) by mole[*1] | 0.03 | 0.03 | 0.03 | 0.03 |
| | Reaction temperature | ° C. | 30 | 30 | 30 | 30 |
| | Purity of epoxy compound | HPLC area % | 35.2 | 79.2 | 24.5 | 20.0 |
| | Yield of epoxy compound | % | [*4] | 85.0 | [*4] | [*4] |

[*1] "Time(s) by mole" means the molar ratio to the molar amount of the amine compound.
[*2] "TBAHS" represents tetra-n-butyl ammonium hydrogen sulfate.
[*3] "—" represents not added.
[*4] Representing that, because of low purity, calculation was not performed.

TABLE 2

| | | | Example 6 | Example 7 | Comparative Example 5 | Comparative Example 6 | Comparative Example 7 | Comparative Example 8 |
|---|---|---|---|---|---|---|---|---|
| Addition reaction | Raw material (amine compound) | | 3,4'-diamino-diphenyl ether | 3,4'-diamino-diphenyl ether | 3,4'-diamino-diphenyl ether | 3,4'-diamino-diphenyl ether | 3,4'-diamino-diphenyl ether | 3,4'-diamino-diphenyl ether |
| | Amount of epichlorohydrin | Time(s) by mole[*1] | 12.0 | 12.0 | 12.0 | 12.0 | 12.0 | 12.0 |
| | Acidic compound | | Acetic acid | Lactic acid | Acetic acid | Acetic acid | Acetic acid | —[*3] |
| | Amount of acidic compound | Time(s) by mole[*1] | 1.5 | 1.5 | 1.5 | 1.5 | 1.5 | — |
| | Solvent | | —[*3] | —[*3] | —[*3] | —[*3] | —[*3] | —[*3] |
| | Amount of solvent | Time(s) by weight | — | — | — | — | — | — |
| | Liquid space velocity | $h^{-1}$ | 0.7 | 0.7 | 20.0 | 0.1 | 0.7 | 0.7 |
| | Reaction temperature | ° C. | 80 | 80 | 80 | 80 | 30 | 80 |
| | Purity of N,N,N',N'-tetra(2-hydroxy-3-chloropropyl)diamine compound | HPLC area % | 93.5 | 93.0 | 30.3 | 52.3 | 7.0 | 0.0 |
| Cyclization reaction | Reaction time | Hour | 2 | 2 | 2 | 2 | 2 | |
| | Kind of catalyst[*2] | | TBAHS | TBAHS | TBAHS | TBAHS | TBAHS | |
| | Amount of catalyst | Time(s) by mole[*1] | 0.03 | 0.03 | 0.03 | 0.03 | 0.03 | |
| | Reaction temperature | ° C. | 30 | 30 | 30 | 30 | 30 | |
| | Purity of epoxy compound | HPLC area % | 91.8 | 86.7 | 41.7 | 63.3 | 27.5 | |
| | Yield of epoxy compound | % | 94.6 | 95.8 | [*4] | 97.7 | [*4] | |

[*1] "Time(s) by mole" means the molar ratio to the molar amount of the amine compound.
[*2] "TBAHS" represents tetra-n-butyl ammonium hydrogen sulfate.
[*3] "—" represents not added.
[*4] Representing that, because of low purity, calculation was not performed.

TABLE 3

|  |  |  | Example 8 | Comparative Example 9 | Comparative Example 10 | Comparative Example 11 | Comparative Example 12 |
|---|---|---|---|---|---|---|---|
| Addition reaction | Raw material (amine compound) |  | m-amino phenol | m-amino phenol | m-amino phenol | m-amino phenol | m-amino phenol |
|  | Amount of epichlorohydrin | Time(s) by mole*1 | 9.0 | 9.0 | 9.0 | 9.0 | 9.0 |
|  | Acidic compound |  | Acetic acid | Acetic acid | Acetic acid | Acetic acid | —*3 |
|  | Amount of acidic compound | Time(s) by mole*1 | 1.5 | 1.5 | 1.5 | 1.5 | — |
|  | Solvent |  | —*3 | —*3 | —*3 | —*3 | —*3 |
|  | Amount of solvent | Time(s) by weight | — | — | — | — | — |
|  | Liquid space velocity | h$^{-1}$ | 1.4 | 20.0 | 0.1 | 1.4 | 1.4 |
|  | Reaction temperature | °C. | 70 | 70 | 70 | 30 | 70 |
|  | Purity of N,N-bis(2-hydroxy-3-chloropropyl)amine compound | HPLC area % | 98.1 | 59.4 | 77.7 | 87.1 | 74.8 |
| Cyclization reaction | Reaction time | Hour | 2 | 2 | 2 | 2 | 2 |
|  | Kind of catalyst*2 |  | — | TBAHS | TBAHS | TBAHS | TBAHS |
|  | Amount of catalyst | Time(s) by mole*1 | — | 0.03 | 0.03 | 0.03 | 0.03 |
|  | Reaction temperature | °C. | 40 | 30 | 30 | 30 | 30 |
|  | Purity of epoxy compound | HPLC area % | 72.0 | 48.4 | 39.8 | 46.3 | 58.2 |
|  | Yield of epoxy compound | % | 84.0 | 69.4 | 60.7 | 65.7 | 71.1 |

*1"Time(s) by mole" means the molar ratio to the molar amount of the amine compound.
*2"TBAHS" represents tetra-n-butyl ammonium hydrogen sulfate.
*3"—" represents not added.
*4Representing that, because of low purity, calculation was not performed.

TABLE 4

|  |  |  | Example 9 | Comparative Example 13 | Comparative Example 14 | Comparative Example 15 | Comparative Example 16 |
|---|---|---|---|---|---|---|---|
| Addition reaction | Raw material (amine compound) |  | 4,4'-diamino-diphenyl methane | 4,4'-diamino-diphenyl Methane | 4,4'-diamino-diphenyl methane | 4,4'-diamino-diphenyl methane | 4,4'-diamino-diphenyl methane |
|  | Amount of epichlorohydrin | Time(s) by mole*1 | 12.0 | 12.0 | 12.0 | 12.0 | 12.0 |
|  | Acidic compound |  | Acetic acid | Acetic acid | Acetic acid | Acetic acid | —*3 |
|  | Amount of acidic compound | Time(s) by mole*1 | 1.5 | 1.5 | 1.5 | 1.5 | — |
|  | Solvent |  | —*3 | —*3 | —*3 | —*3 | —*3 |
|  | Amount of solvent | Time(s) by weight | — | — | — | — | — |
|  | Liquid space velocity | h$^{-1}$ | 1.4 | 20.0 | 0.1 | 1.4 | 1.4 |
|  | Reaction temperature | °C. | 80 | 80 | 80 | 30 | 80 |
|  | Purity of N,N,N',N'-tetra(2-hydroxy-3-chloropropyl)diamine compound | HPLC area % | 93.9 | 16.8 | 51.7 | 18.6 | 0.0 |
| Cyclization reaction | Reaction time | Hour | 2 | 2 | 2 | 2 |  |
|  | Kind of catalyst*2 |  | TBAHS | TBAHS | TBAHS | TBAHS |  |
|  | Amount of catalyst | Time(s) by mole*1 | 0.03 | 0.03 | 0.03 | 0.03 |  |
|  | Reaction temperature | °C. | 30 | 30 | 30 | 30 |  |
|  | Purity of epoxy compound | HPLC area % | 90.0 | 25.3 | 56.9 | 54.6 |  |
|  | Yield of epoxy compound | % | 88.4 | *4 | 100.0 | 85.8 |  |

*1"Time(s) by mole" means the molar ratio to the molar amount of the amine compound.
*2"TBAHS" represents tetra-n-butyl ammonium hydrogen sulfate.
*3"—" represents not added.
*4Representing that, because of low purity, calculation was not performed.

TABLE 5

|  |  |  | Example 10 | Comparative Example 17 | Comparative Example 18 | Comparative Example 19 | Comparative Example 20 |
|---|---|---|---|---|---|---|---|
| Addition reaction | Raw material (amine compound) |  | Aniline | Aniline | Aniline | Aniline | Aniline |
|  | Amount of epichlorohydrin | Time(s) by mole*1 | 6.0 | 6.0 | 6.0 | 6.0 | 6.0 |
|  | Acidic compound |  | Acetic acid | Acetic acid | Acetic acid | Acetic acid | —*3 |
|  | Amount of acidic compound | Time(s) by mole*1 | 1.5 | 1.5 | 1.5 | 1.5 | — |
|  | Solvent |  | —*3 | —*3 | —*3 | —*3 | —*3 |

TABLE 5-continued

|  |  |  | Example 10 | Comparative Example 17 | Comparative Example 18 | Comparative Example 19 | Comparative Example 20 |
|---|---|---|---|---|---|---|---|
|  | Amount of solvent | Time(s) by weight | — | — | — | — | — |
|  | Liquid space velocity | h$^{-1}$ | 1.4 | 20.0 | 0.1 | 1.4 | 1.4 |
|  | Reaction temperature | ° C. | 70 | 70 | 70 | 30 | 70 |
|  | Purity of N,N-bis(2-hydroxy-3-chloropropyl)amine compound | HPLC area % | 98.6 | 74.1 | 86.8 | 80.7 | 0.0 |
| Cyclization reaction | Reaction time | Hour | 2 | 2 | 2 | 2 |  |
|  | Kind of catalyst*$^{2}$ |  | TBAHS | TBAHS | TBAHS | TBAHS |  |
|  | Amount of catalyst | Time(s) by smole*$^{1}$ | 0.03 | 0.03 | 0.03 | 0.03 |  |
|  | Reaction temperature | ° C. | 30 | 30 | 30 | 30 |  |
|  | Purity of epoxy compound | HPLC area % | 96.0 | 72.6 | 89.9 | 94.1 |  |
|  | Yield of epoxy compound | % | 93.9 | 74.3 | 97.9 | 82.8 |  |

*$^{1}$"Time(s) by mole" means the molar ratio to the molar amount of the amine compound.
*$^{2}$"TBAHS" represents tetra-n-butyl ammonium hydrogen sulfate.
*$^{3}$"—" represents not added.
*$^{4}$Representing that, because of low purity, calculation was not performed.

The invention claimed is:

1. A method of manufacturing a compound having an N,N-bis(2-hydroxy-3-chloropropyl)amino group in which (1) an amine compound or a solution thereof, (2) epichlorohydrin or a solution thereof, and (3) an acidic compound or a solution thereof are continuously supplied to a flow reactor and reacted at a reaction temperature of 60 to 115° C. and a liquid space velocity of 0.5 to 5 h$^{-1}$.

2. The method according to claim 1, wherein a tubular reactor is used as the flow reactor.

3. The method according to claim 2, wherein the tubular reactor is charged with a filler.

4. The method according to claim 1, wherein the acidic compound is a Lewis acid or an organic acid.

5. The method according to claim 1, wherein, as the amine compound, one selected from the group consisting of aniline, toluidine, phenoxy aniline, amino phenol, diaminodiphenyl ether, diaminodiphenyl methane, and diaminodiphenyl sulphone is used.

6. A method of manufacturing a polyfunctional glycidylamine type epoxy compound comprising producing the compound having an N,N-bis(2-hydroxy-3-chloropropyl) amino group manufactured according to claim 1 and dehydrochlorinating the obtained compound having the N,N-bis (2-hydroxy-3-chloropropyl)amino group with an alkali to produce the polyfunctional glycidylamine type epoxy compound.

7. The method according to claim 2, wherein the acidic compound is a Lewis acid or an organic acid.

8. The method according to claim 3, wherein the acidic compound is a Lewis acid or an organic acid.

9. The method according to claim 2, wherein, as the amine compound, one selected from the group consisting of aniline, toluidine, phenoxy aniline, amino phenol, diaminodiphenyl ether, diaminodiphenyl methane, and diaminodiphenyl sulphone is used.

10. The method according to claim 3, wherein, as the amine compound, one selected from the group consisting of aniline, toluidine, phenoxy aniline, amino phenol, diaminodiphenyl ether, diaminodiphenyl methane, and diaminodiphenyl sulphone is used.

11. The method according to claim 4, wherein, as the amine compound, one selected from the group consisting of aniline, toluidine, phenoxy aniline, amino phenol, diaminodiphenyl ether, diaminodiphenyl methane, and diaminodiphenyl sulphone is used.

12. A method of manufacturing a polyfunctional glycidylamine type epoxy compound comprising producing the compound having an N,N-bis(2-hydroxy-3-chloropropyl) amino group manufactured according to claim 2 and dehydrochlorinating the obtained compound having the N,N-bis (2-hydroxy-3-chloropropyl)amino group with an alkali to produce the polyfunctional glycidylamine type epoxy compound.

13. A method of manufacturing a polyfunctional glycidylamine type epoxy compound comprising producing the compound having an N,N-bis(2-hydroxy-3-chloropropyl) amino group manufactured according to claim 3 and dehydrochlorinating the obtained compound having the N,N-bis (2-hydroxy-3-chloropropyl)amino group with an alkali to produce the polyfunctional glycidylamine type epoxy compound.

14. A method of manufacturing a polyfunctional glycidylamine type epoxy compound comprising producing the compound having an N,N-bis(2-hydroxy-3-chloropropyl) amino group manufactured according to claim 4 and dehydrochlorinating the obtained compound having the N,N-bis (2-hydroxy-3-chloropropyl)amino group with an alkali to produce the polyfunctional glycidylamine type epoxy compound.

15. A method of manufacturing a polyfunctional glycidylamine type epoxy compound comprising producing the compound having an N,N-bis(2-hydroxy-3-chloropropyl) amino group manufactured according to claim 5 and dehydrochlorinating the obtained compound having the N,N-bis (2-hydroxy-3-chloropropyl)amino group with an alkali to produce the polyfunctional glycidylamine type epoxy compound.

* * * * *